United States Patent [19]

Fusey

[11] 4,005,043
[45] Jan. 25, 1977

[54] PREPARATION OF COMPOSITION FOR CONVERTING HYDROCARBONS AND FATS INTO BIODEGRADABLE AQUEOUS EMULSIONS

[76] Inventor: Pierre Fusey, 8 Rue l'Abbe de l'Epee, Paris 5eme, France

[22] Filed: July 25, 1975

[21] Appl. No.: 599,164

[30] Foreign Application Priority Data

July 25, 1974 France .............................. 74.25835

[52] U.S. Cl. .............................. 252/356; 252/354; 252/355; 252/357; 252/DIG. 6
[51] Int. Cl.² .......................................... B01F 17/00
[58] Field of Search ................... 252/356–357, 252/117–118, 545–546, DIG. 6, 354

[56] References Cited

UNITED STATES PATENTS

| | | | |
|---|---|---|---|
| 1,598,664 | 9/1926 | Teach | 252/118 |
| 1,833,899 | 12/1931 | Hoyt | 252/117 |
| 2,208,524 | 7/1940 | Darsey | 252/118 |
| 3,900,421 | 8/1975 | Fusey | 252/312 |

OTHER PUBLICATIONS

McCutcheon: *Detergents and Emulsifiers;* J. W. McCutcheon, Inc.; 1967, pp. 102, 100.
Felicione, Raw Material Index Chemical Specialties Sec., National Paint Varnish & Lacquer Assoc., Inc., 1967 V. 3, pp. 829–830.
Booman et al.: "Degradation Studies on Branched Chain EO Surfactants", Soap and Chemical Specialties, Jan. 1965, p. 60.
Morrison and Boyd: *Organic Chemistry;* Allyn and Bacon, 1966, p. 669.
*Chemical Abstracts,* vol. 80 (1974) p. 228, No. 6664t, Jan. 14, 1974.

*Primary Examiner*—Leland A. Sebastian
*Attorney, Agent, or Firm*—Young & Thompson

[57] ABSTRACT

The present invention concerns a process for the preparation of a composition for converting hydrocarbons and fats into biodegradable aqueous emulsions and the composition thus obtained. At least one straight or branched chain monobasic carboxylic acid is reacted at ambient temperature with a less than equimolecular quantity of a nitrogen compound selected from tertiary alkylamines, tertiary alkanolamines and ammonia, the pH of the reaction medium is adjusted to a value of 7 to 9 and the composition thus obtained is diluted with a benzene-free petroleum solvent or water. Said composition preferably with added phospho-amino-lipid is used to put the hydrocarbons and fats in the form of a biodegradable emulsion.

7 Claims, No Drawings

PREPARATION OF COMPOSITION FOR CONVERTING HYDROCARBONS AND FATS INTO BIODEGRADABLE AQUEOUS EMULSIONS

This invention relates to the preparation of a composition for converting hydrocarbons and fats into biodegradable aqueous emulsions.

The elimination of unwanted hydrocarbons and fats by biological degradation presents problems since the natural biodegradation rate thereof is very slow. In order to accelerate the biodegradation of hydrocarbons and of crude petroleum by microorganisms, it is necessary to provide the microorganisms with nitrogen and phosphorus which when added to the carbon of the products to be eliminated will enable the microorganisms to multiply.

When the biodegradation is carried out in a closed environment, i.e. in a fermentation vessel or vat, it is sufficient to employ an aqueous culture medium containing the various elements either in solution or in suspension. On the other hand, investigation have shown that when working in a highly dilute medium, for example when discharged into the sea or a river, the substances supplying the nitrogen and the phosphorus should be linked to the hydrocarbon molecules to form an emulsion therewith, failing which the substances will be diluted to an extent effectively equal to the natural content of these substances in water, with the result that the rate of degradation reverts to the natural speed of biodegradation.

It is therefore necessary for the product to be removed by biodegradation to be converted into an aqueous emulsion, the emulsifiable molecules containing, in addition to those of the product to be degraded, molecules of substances which will supply nitrogen and preferably phosphorus.

The composition formed by substances supplying nitrogen and phosphorus should also be sufficiently detersive to ensure that surfaces contaminated by the products to be removed are cleaned, but since the object is to accelerate the biodegradation of the emulsion the constituents thereof should not be watersoluble in order to ensure that the nutritional completement that they represent remains. It is also necessary that the composition should not itself be toxic to plants or animals.

Investigations have shown that magnesium is an element which is indispensable to bacteria which digest hydrocarbons. Generally speaking, the magnesium content of the medium into which the oil is discharged, whether sea or running water, is sufficient to make the necessary magnesium available to the bacteria, but if the risk of any insufficiency arises it is preferable to add some magnesium to the emulsifying composition in the form of a salt which must be soluble in the hydrocarbons in order to prevent it being dispersed in the aqueous discharge medium and to maintain it in an available state to the bacteria in the emulsified molecule.

U.S. Pat. No. 3,943,066 describes a composition for converting hydrocarbons and fats into aqueous emulsions, which composition essentially comprises an alkyl amide or a carboxylic ester of an alkyl amide acting as a detergent. This composition is prepared by reacting an excess of the carboxylic acid with a primary or secondary alkyl amine or a primary or secondary alkanolamine, the excess of acid being neutralised with ammonia. The detergent part of the composition therefore essentially comprises an alkyl mono- or di-amide or a carboxylic ester of such an alkyl mono- or di-amide together with a smaller quantity of an ammonium carboxylate. The composition described in the above application also contains small quantities of a phospho-aminolipid which dissolves in the hydrocarbons to provide a quantity of nitrogen additional to that from the amides and especially the phosphorus necessary for the proliferation of the bacteria, and a benzene-free non-toxic petroleum solvent for diluting the unwanted hydrocarbons and fats and for providing a carrier for the alkyl amides or esters of such alkyl amides and the phospho-aminolipid.

The mono- and di-amides of which the composition described in U.S. Pat. No. 3,943,066 is essentially composed are much less toxic than known detergents. In fact, while the CL50 (median lethal concentration) to Daphnia magna used to evaluate the toxicity of detergents is from 1.5 to 1.7 ppm for the least toxic of the known detergents, the detergent described in this application has a value of from 50 to 60 ppm. However, this toxicity is an extremely important factor in the quality of biodegradable detergents since the toxicity of the detergent concentration is added to that resulting from the hydrocarbon concentration in the dilution medium.

Accordingly if the detergent producing a biodegradable emulsion of the hydrocarbon is to produce a dispersion of the latter in the form of emulsified droplets containing the nitrogen and phosphorus needed by the bacteria, it must not itself, and in the concentrations which can be produced, be toxic to animals and plants.

A further important characteristic of these detergents is the acceptable organoleptic concentration in drinking water. Although hydrocarbons do not give any taste at concentrations below 0.5 ppm, in the case of phenolic detergents this limiting concentration falls below 0.005 ppm. The acceptable or permissible detergent concentration is therefore an essential feature from the point of view of the taste of the water.

The present invention in one aspect provides a process for preparing a composition for converting hydrocarbon oils, greases and fats into aqueous biodegradable emulsions, comprising reacting at least one straight- or branched chain monobasic carboxylic acid at ambient temperature with a less than equimolecular quantity of a nitrogen compound selected from tertiary alkyl amines, tertiary alkanolamines and ammonia, adjusting the reaction medium to a pH of from 7 to 9, and diluting the composition thus obtained with a benzene-free petroleum solvent or water.

Phosphorus in the form of a phospho-aminolipid is preferably added to the reaction mass. The phospho-aminolipid is preferably lecithin.

In the process according to the invention, when the nitrogen compound is ammonia the carboxylic acid is a $C_3$ to $C_{18}$ carboxylic acid such as lactic, hexanoic, ethyl-2-hexanoic, octanoic, lauric, palmitic, linoleic, oleic, stearic or ricinoleic acid.

When the nitrogen compound is a tertiary alkyl amine the carboxylic acid is a $C_3$ to $C_{10}$ monobasic carboxylic acid such as lactic, hexanoic, ethyl-2-hexanoic or octanoic acid.

When the nitrogen compound is a tertiary alkanolamine the carboxylic acid is selected according to the length of the alkyl chain of the alkanolamine in order that the number of carbon atoms in the resulting ester chain should be less than 10. For example when the nitrogen compound is triethanolamine the carboxylic acid is a $C_3$ to $C_8$ aliphatic carboxylic acid as lactic, hexanoic, ethyl-2-hexanoic or octanoic acid.

The tertiary amine preferably has a $C_1$ to $C_{10}$, more preferably a $C_1$ to $C_4$, carbon chain, and is for example trimethylamine, triethylamine, tripropylamine or tributylamine.

The tertiary alkanolamine is preferably triethanolamine.

The benzene-free petroleum solvent is suitably benzene-free white spirit, n-hexane, n-heptane, n-octane, petrol ether, benzene-free heavy solvent or a mixture of these solvents.

The choice of diluent depends on the starting materials and particularly on the number of carbon atoms in the resulting composition and on the pH value. All the products obtained must be adjusted to a pH of from 7 to 7.5; they are then soluble in petroleum solvents. At a pH of from 8.5 to 9, products in which the radical R or R' contains 8 carbon atoms and more are dispersible in water. At a pH in the region of 8.5, products in which the radical R or R' contains less than 8 carbon atoms are soluble in water.

The resulting composition for converting hydrocarbon oils, greases and fats into biodegradable emulsions, comprises an ammonium salt of a carboxylic acid of the formula:

or of the composition:

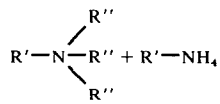

wherein R is a straight or branched chain alkyl radical of $C_3$ to $C_{18}$ carboxylic acid, R' is a straight or branched chain alkyl radical of a $C_3$ to $C_{10}$ carboxylic acid, and R" is an alkyl radical or an alkanol radical, R" containing from 1 to 10 carbon atoms.

The number of carbon atoms in the alkyl chains is limited to obtain an emulsifier suitable for use as a detergent after solution in a petroleum solvent or dispersion in water. When the carboxylic acid has a chain less than $C_8$ the emulsifier is soluble in water. Although such a composition is effective as a detergent the emulsion is not stable, with the result that the product is less suitable for the biodegradable emulsification of heavy hydrocarbons.

When R" is an alkanol radical it may be esterified with a carboxylic acid having a $C_3$ to $C_{10}$ straight- or branched chain radical.

The composition also preferably contains from 2 to 10 % of a source of phosphorus in the form of a phospho-aminolipid.

The diluent is added in the desired amount so as to produce the required fluidity, either during the preparation of the composition or immediately prior to its use.

The composition preferably contains from 3 to 10 % of the combined weight of the ammonium salt and source of phosphorus, of at least one non-toxic and completely biodegradable emulsifier such as sodium oleylisethionate, a sarcosinate, 2-amino-2-hydroxymethyl-1,3-propanediol, aminomethylpropanol, non toxic ethoxylated fatty alcohols, non-toxic ethoxylated fatty acids and polyoxyethylene glycol oleate. The object of this emulsifier is to stabilize the hydrocarbon emulsion obtained in water.

The composition may also contain from 0.5 to 3 % of magnesium salts in the form of organic salts.

The toxicity of the compositions according to the invention has been measured in the form of their CL 50 on Daphnia magna. It is about 600 ppm for salts of formula $R-NH_4$. It is about 280 ppm for tertiary amine salts and it reaches a value of 750 ppm for salts of partially esterified alkanolamines. The CL 50 for fish are very high, being about 300 ppm for minnows and about 3000 ppm for carp.

As far as the organoleptic character is concerned, 5 ppm imparts no taste to drinking water, which is superior to known detergents.

The invention will be further described with reference to the following illustrative Examples. In the Examples all parts and percentages are by weight.

GROUP 1 — COMPOSITIONS BASED ON AMMONIUM SALTS OF THE FORMULA $R-NH_4$.

A. COMPOSITIONS DILUTED WITH A PETROLEUM SOLVENT.

EXAMPLE 1

30 parts of oleic acid were mixed with 0.5 parts of lecithin and the mixture was neutralised with about 6 parts of 22° Be ammonia to adjust to a pH of from 7 to 7.5, and then white spirit was added to make the composition up to 150 parts.

The detergent liquid obtained was used to clean by immersion pieces of machinery, resulting in the removal from the pieces of the contaminating oils.

EXAMPLE 2

30 parts of oleic acid were mixed with 0.5 parts of lecithin and the mixture was neutralised with about 6 parts of 22° Be ammonia to adjust to a pH of from 7 to 7.5. 2 parts by weight of an emulsifier consisting of polyoxyethyleneglycol oleate and 1 part of magnesium stearate were then added. The composition was then made up to 150 parts with n-hexane.

Wiping cloths soiled with grease were steeped in the composition and then rinsed in water containing a small quantity of magnesium salts. The cloths came out clean and the water contained a fine emulsion of the grease; the emulsion was found to be very stable. The rinsing water was seeded with microorganisms of the Aspergillus carbonarius type. The biodegradation of the hydrocarbons, measure by weighed extraction, was found to be five times more rapid than normal.

EXAMPLE 3

30 parts of octanoic acid (caprylic acid) were mixed with 0.5 parts of lecithin and the mixture was neutralised with about 11 parts of 22° Be ammonia to adjust to a pH of from 7 to 7.5 The reaction mixture of ammonium octanoate and lecithin was dissolved in petrol ether. The composition was used to clean soil contaminated by accumulations of fuel No. 2 long since oxidised. The washing water containing the emulsion was recovered and its non-toxicity to plants and animals and biodegradability was confirmed.

EXAMPLE 4

60 parts of ethyl-2-hexanoic acid were mixed with 1 part of soya lecithin and the mixture was neutralised with about 24 parts of 22° Be ammonia to adjust to a pH of from 7 to 7.5 and 8 parts of amino-methylpropanol were then added to the mixture of ammonium ethyl-2-hexanoate and lecithin, which was then diluted with twice its weight of white spirit.

The resulting composition was used to scrub quay walls soiled with petroleum deposits. The rinsing water formed a fine emulsion which was disposed of without any harmful effects being observed on animals and plants.

B. COMPOSITIONS DISPERSED IN WATER.

EXAMPLE 5

8 parts of amino-methylpropanol were added to the mixture of ammonium ethyl-2hexanoate and lecithin of Example 4, the resulting composition being used in a mixing ratio of 10% to supply a mixing pump fed with river water. The resulting aqueous emulsion was directed in the form of a jet against a river bank contaminated with heavy fuel No. 2. The heavy fuel was carried away in the form of an aqueous emulsion. No effect was observed on the vegetation on the bank nor was any poisoning observed of the plant and animal life of the river.

The rate of dilution of the composition may vary between 5 and 50%.

EXAMPLE 6

A composition was prepared as described in Example 2, but with the n-hexane omitted. the composition was adjusted to a pH of from 8.5 to 9 by a further addition of ammonia and was used in the same manner as in Example 5 and with the same results.

C. COMPOSITIONS USING WATER AS SOLVENT.

EXAMPLE 7

60 parts of ethyl-2-hexanoic acid were mixed with about 42 parts of 22° Be ammonia until a pH of from 8.5 to 9 was obtained and the mixture was dissolved in sufficient water to make up the composition to 200 parts.

The resulting composition formed an excellent detergent which could be diluted with water as required and which was found to be non-toxic to Daphnia below a concentration of 500 ppm.

EXAMPLE 8

The pH of 40 parts of n-hexanoic acid was adjusted to from 8.5 to 9 with about 48 parts of ammonia. 5 parts of ethoxylated oleic acid (9 OE) were added and dissolved in sufficient water to make up the composition to 200 parts.

The composition had the same characteristics as the composition described in Example 7, but the aqueous emulsion obtained by the action of this composition on petroleum deposits was more stable.

EXAMPLE 9

A composition was prepared as described in Example 8 except that the n-hexanoic acid, was replaced by lactic acid and the mixture was neutralised with ammonia until a pH of 7.5 was obtained. After solution in water the composition was found to form an efficient detergent against grease deposits.

II. COMPOSITIONS BASED ON AMINE SALTS OF THE FORMULA R'-N-R''$_3$.

In these Examples, a slight molar excess of the acid was reacted with the tertiary amine in order to quaternise the nitrogen and the product was neutralised with ammonia.

EXAMPLE 10

50 parts of ethyl-2-hexanoic acid were reacted with 30 parts of triethylamine and 1 part of lecithin was added, resulting in a mixture of triethylamine ethyl-2-hexanoate and lecithin with an excess of ethyl-2-hexanoic acid. The reaction mixture was neutralised with 22° Be ammonia to adjust to a pH of from 7 to 7.5

The mixture was diluted with substantially an equal amount of white spirit, resulting in a detergent composition forming with greases and hydrocarbon oils a stable oil/water biodegradable emulsion.

EXAMPLE 11

60 parts of octanoic acid were reacted with 20 parts of trimethylamine, and 1 part of lecithin was then added. The pH of the reaction mixture was then adjusted to from 7 to 7.5 with 22° Be ammonia, and petrol ether was then added to make up the composition to 150 parts. A detergent composition was obtained having the same properties as that described in Example 10.

EXAMPLE 12

55 parts of ethyl-2-hexanoic acid were reacted with 30 parts of tributylamine, and 1 part of lecithin was then added. The mixture was neutralised with sufficient 22° Be ammonia, the composition was made up to 150 parts with n-hexane, and 6% of polyoxyethylene glycol oleate was then added. A detergent composition was obtained having the same properties as that described in Example 7.

III. COMPOSITIONS BASED ON SALTS OF ESTERIFIED ALKANOLAMINES

In these Examples the acid was reacted with the alkanolamine employing a 40 to 70% excess of acid in order to partially esterify the alcohol group.

EXAMPLE 13

65 parts of ethyl-2-hexanoic acid were reacted with 15 parts of triethanolamine and 1 part of lecithin was added to the reaction mixture. The mixture was then neutralised with about 7 parts of 22° Be ammonia to adjust the pH to 7.5, and 8 parts of polyoxyethyleneglycol oleate were then added.

The composition was used in the form of a 10 % dispersion in sea water by using it in situ in the form of a jet for cleaning shingly beaches contaminated with oxidised hydrocarbon oils. The oil was disposed of, the emulsion formed being dispersed naturally by the tide leaving no trace of pollution on animals and vegetation in the neighbourhood. No redeposition of oil was found to occur in the neighbourhood, thus confirming the high stability of the emulsion.

The composition in which the 8 parts of polyethylene glycol oleate were substituted by 4 parts of sodium oleylisethionate, 2 parts of 2-amino-2-hydroxymethyl-1,3-propanediol and 2 parts of sodium sarcosinate was used in a similar manner to clean ship's hulls and bottoms contaminated with patches of oil, and also factory floors stained with patches of mineral and animal grease.

The CL 50 of the composition measured on Daphnia magna was found to be about 750 ppm and about 3000 ppm for Cyprinid species (carp.)

EXAMPLE 14.

65 parts of octanoic acid were reacted with 15 parts of triethanolamine, to which was added 1 part of lecithin, and the mixture was then brought to a pH of 7.5 by the addition of 22° Be ammonia. The mixture was diluted with white spirit, resulting in a composition having properties similar to those of the composition described in Example 10.

EXAMPLE 15.

12 parts of hexanoic acid were reacted with 7 parts of triethanolamine, and then a sufficient quantity of 22° Be ammonia was added to adjust the pH to 7.5.

The resulting composition was soluble in water. When diluted in a proportion of 1 part to 50 parts of water, the composition was found to be an effective detergent for washing boiler suits.

EXAMPLE 16.

A composition was prepared as described in Example 15 except that the 12 parts of hexanoic acid were replaced by 18 parts of lactic acid. The pH was adjusted to 7.5 by the addition of ammonia, yielding a detergent composition having the same properties as that described in Example 15.

What we claim is:

1. A process for the preparation of a composition for forming hydrocarbons or fats into a biodegradable emulsion, comprising admixing at ambient temperature more than one mole of a $C_6 - C_8$ carboxylic acid with a mole of a nitrogen compound selected from the group consisting of tertiary alkyl amines and tertiary alkanolamines, with the addition of 2 to 10% by weight of the composition of lecithin, adding ammonia to bring the mixture to a pH of from 7 to 9, and diluting the composition thus formed with a benzene-free petroleum solvent or water.

2. A process as claimed in claim 1, in which said phosphoaminolipid is lecithin.

3. A process as claimed in claim 1, in which said nitrogen compound is a $C_1 - C_4$ tertiary alkyl amine.

4. A process as claimed in claim 1, in which said nitrogen compound is triethanolamine.

5. A process as claimed in claim 1, in which said carboxylic acid is a $C_8$ carboxylic acid.

6. A process as claimed in claim 5, in which said carboxylic acid is octanoic acid.

7. A process as claimed in claim 5, in which said carboxylic acid is 2-ethylhexanoic acid.

* * * * *